United States Patent

Nambu et al.

[11] 4,239,644
[45] Dec. 16, 1980

[54] LIQUID PEROXIDE COMPOSITION

[75] Inventors: Hirohiko Nambu, Iwakuni; Kenichi Mizuno; Tetuhiro Matumoto, both of Otake, all of Japan

[73] Assignee: Mitsui Petrochemical Industries Ltd., Tokyo, Japan

[21] Appl. No.: 22,499

[22] Filed: Mar. 21, 1979

[51] Int. Cl.³ .................. C08C 19/04; C08F 8/06; C07C 179/14
[52] U.S. Cl. ...................... 252/186; 252/95; 525/387; 562/558; 562/578
[58] Field of Search .................. 252/186, 95; 568/558, 568/578; 525/387; 526/67

[56] References Cited

U.S. PATENT DOCUMENTS

| 2,668,180 | 2/1954 | Boardman | 568/558 |
| 2,819,255 | 1/1958 | Boardman | 568/558 |
| 2,819,256 | 1/1958 | Boardman | 525/387 |
| 2,826,570 | 3/1958 | Ivett | 525/387 |
| 2,994,719 | 8/1961 | Farkas | 568/588 |

Primary Examiner—Benjamin R. Padgett
Assistant Examiner—Irwin Gluck
Attorney, Agent, or Firm—Sherman & Shalloway

[57] ABSTRACT

A liquid peroxide composition comprising dicumyl peroxide and a dicumyl peroxide derivative having one nucleus substituted by an alkyl group having 1 to 3 carbon atoms is disclosed. This peroxide composition can easily be handled because it is liquid, and it is very valuable as a cross-linking agent for an olefin polymer or a synthetic rubber.

8 Claims, 1 Drawing Figure

LIQUID PEROXIDE COMPOSITION

BACKGROUND OF THE INVENTION (1) Field of the Invention

The present invention relates to a novel liquid peroxide composition and a process for the preparation thereof. More particularly, the invention relates to a liquid peroxide composition valuable as a cross-linking agent for a high polymer for electric insulation, and a process for the preparation thereof.

(2) Description of the Prior Art

Electrically insulating layers for wires, cables and the like are ordinarily formed by extruding on a conductor a composition comprising high-pressure polyethylene and an appropriate amount of an organic peroxide cross-linking agent to form a coating on the conductor and cross-linking the coated composition. In order to carry out cross-linking of polyethylene at high efficiency at the cross-linking step while preventing decomposition of the peroxide cross-linking agent at the extruding and coating step, dicumyl peroxide (hereinafter abbreviated to "DCP") which has excellent properties as the organic peroxide cross-linking agent and is cheap is mainly used in this field. However, even DCP still involves problems to be solved or defects to be eliminated. At the step of kneading polyethylene with DCP, the use of an extruder is ordinarily preferred from the viewpoint of the operation efficiency, but when the extruder is used at the kneading step, in order to obtain a homogeneous composition, it is necessary to feed DCP at a constant speed. For this purpose, DCP which is normally in the form of a solid inferior in the metering property should be molten to render it liquid. This requires provision of a particular device for melting DCP and furthermore, this results in a disadvantage that since DCP is maintained in the high-temperature molten state, loss of DCP is caused by decomposition and a special care should be paid to maintenance of the safety. Furthermore, when solid DCP is handled, incorporation of different matter is hardly avoided, and different matter having bad influences on the quality of the insulating layer should be removed in advance. Therefore, such troublesome operation as filtration after melting should be inevitably conducted.

Of course, liquid peroxides are known in the art. However, known liquid peroxides such as α,α-dimethylbenzyl(α,α-dimethyl-p-isopropylbenzyl)peroxide disclosed in the specifications of U.S. Pat. No. 2,819,256 and U.S. Pat. No. 2,826,570 are still insufficient and defective in that the gel proportion of a cross-linked polymer obtained by incorporating such liquid peroxide into a polymer so that an active oxygen amount is constant is much lower than the gel proportion attained by DCP. In short, these known liquid peroxides are still unsatisfactory in the cross-linking efficiency.

SUMMARY OF THE INVENTION

We made extensive researches with a view to developing an organic peroxide having cross-linking characteristics comparable to those of DCP and being in the form of a liquid that can easily be handled, and as a result, it was found that a composition comprising dicumyl peroxide and a dicumyl peroxide derivative having one nucleus substituted by an alkyl group having 1 to 3 carbon atoms at a specific ratio meets the above-mentioned requirements.

It is therefore a primary object of the present invention to provide a peroxide composition which is liquid at room temperature and has cross-linking characteristics comparable to those of dicumyl peroxide.

Another object of the present invention is to provide a novel peroxide composition which is excellent over dicumyl peroxide with respect to the adaptability to such operations as metering and feeding to an extruder and which can be mixed with a high polymer in an extruder or the like more easily than dicumyl peroxide and hence, can provide a cross-linked extrusion-molded article having excellent quality.

Still another object of the present invention is to provide a process in which the above-mentioned liquid peroxide composition can be prepared very easily.

In accordance with the present invention, there is provided a peroxide composition which is liquid at 25° C., comprising (A) dicumyl peroxide and (B) a peroxide represented by the following general formula:

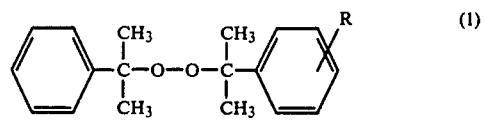

wherein R stands for an alkyl group having 1 to 3 carbon atoms, at an (A)/(B) weight ratio of from 70/30 to 5/95.

In the above general formula (1), it is preferred that the alkyl group R be bonded to the α,α-dimethylcumylperoxymethyl group at the meta- or para-position.

DETAILED DESCRIPTION OF THE PREFERRED EMBODIMENTS

Figure 1:
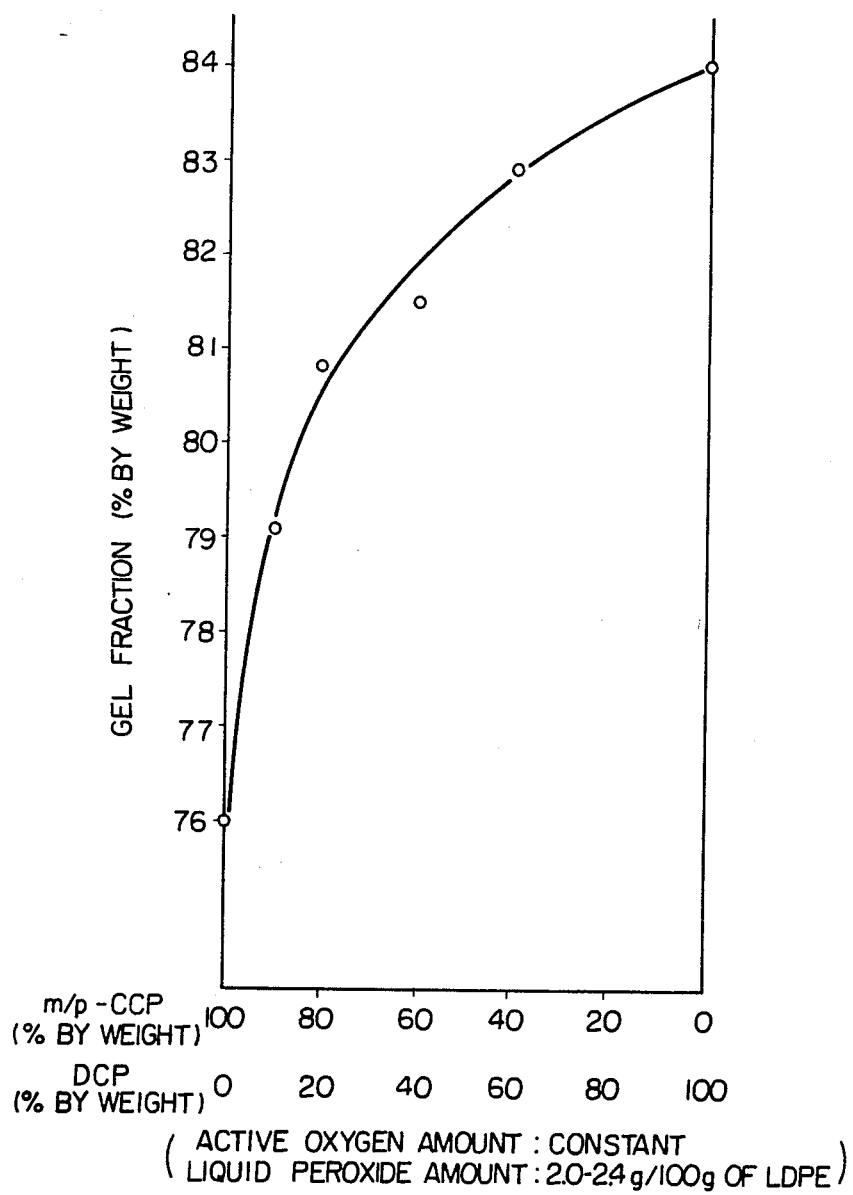
FIG. 1 is a diagram illustrating the relation of the gel fraction (%) of a polymer obtained by cross-linking a composition formed by incorporating in 100 parts by weight of low density polyethylene 2.0 to 2.4 parts by weight of DCP, cumylcymyl peroxide (hereinafter abbreviated to "CCP") or a mixture thereof so that the active oxygen amount is constant, to the DCP/CCP mixing ratio.

The liquid peroxide composition of the present invention comprises (A) dicumyl peroxide and (B) a peroxide represented by the above general formula (1).

As specific examples of the peroxide represented by the general formula (1), there can be mentioned α,α-dimethylbenzyl(α,α-dimethyl-m-methylbenzyl)peroxide, α,α-dimethylbenzyl(α,α-dimethyl-p-methylbenzyl)peroxide, α,α-dimethylbenzyl(α,α-dimethyl-m-ethylbenzyl)peroxide, α,α-dimethylbenzyl(α,α-dimethyl-p-ethylbenzyl)peroxide, α,α-dimethylbenzyl(α,α-dimethyl-m-isopropylbenzyl)peroxide, α,α-dimethylbenzyl(α,α-dimethyl-p-isopropylbenzyl)peroxide, and mixtures thereof.

In order to attain the above-mentioned objects of the present invention, it is especially preferred to select and use, among these peroxides, α,α-dimethylbenzyl(α,α-dimethyl-m-methylbenzyl)peroxide, which is a novel compound not disclosed in any literature reference, α,α-dimethylbenzyl(α,α-dimethyl-p-methylbenzyl)peroxide or a mixture thereof.

In order to attain the foregoing objects of the present invention, it is important that DCP (A) and the peroxide (B) should be mixed at an (A)/(B) weight ratio of from 70/30 to 5/95, especially from 60/40 to 10/90. More specifically, in order to keep the peroxide composition of the present invention in the liquid state at 25° C., the above-mentioned (A)/(B) weight ratio is very important. If the amount of DCP is larger than 70% by weight (all of "%" given hereinafter being by weight), the composition is partially crystallized at 25° C. or the composition becomes too highly viscous, though this critical amount of DCP varies to some extent depending on the kind of the peroxide (B). Therefore, from the viewpoint of the operation adaptability or efficiency, DCP is used in an amount not larger than 70%, especially not larger than 60%. When the amount of the peroxide (B) is larger than 95%, the cross-linking characteristics of the composition are drastically degraded. Therefore, the amount of the peroxide (B) is adjusted to 5 to 95%, especially 10 to 90%.

According to the present invention, by combining DCP with the peroxide (B) represented by the general formula (1) at the above-mentioned specific weight ratio, the cross-linking efficiency can be synergistically enhanced as compared with the cross-linking efficiency attainable by the single use of DCP or the peroxide (B). This will readily be understood from experimental results shown in FIG. 1. More specifically, from FIG. 1, it will readily be understood that when DCP and CCP are combined and used at a weight ratio specified in the present invention, cross-linking is caused at a ratio (gel fraction) higher than the arithemtic mean of the values attained by the single use of DCP and CCP. Incidentally, the gel fraction(%) referred to in the instant specification is a value determined according to the known method, that is, a proportion of the insoluble substance measured when a cross-linked polymer is dipped for 24 hours in xylene maintained at 110° C.

From the viewpoint of easiness in handling, it is preferred that the viscosity of the liquid peroxide composition of the present invention be 10 to 50 centipoises, especially 15 to 35 centipoises, as measured at 25° C. by a Brookfield viscometer.

The peroxide composition of the present invention may contain as an impurity a peroxide represented by the following formula:

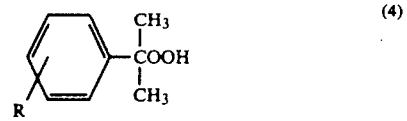

wherein R is as defined above.

The liquid peroxide composition of the present invention may be formed by mixing DCP with a peroxide of the formula (1) prepared separately from DCP. It is preferred that DCP and a peroxide of the formula (1) be prepared in one reaction vessel so that the above-mentioned mixing weight ratio is attained, because the mixing operation can be omitted. A most preferred process comprises reacting cumene hydroperoxide with a mixture of (C) α,α-dimethylbenzyl alcohol and (D) an alcohol represented by the following formula:

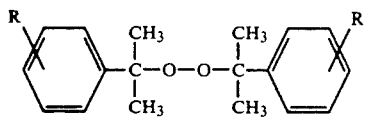

wherein R is as defined above, in the presence of an acid catalyst. The weight ratio (C)/(D) between the two alcohols is selected so that the above-mentioned (A)/(B) weight ratio is attained in the resulting peroxide composition. Ordinarily, it is preferred that the weight ratio (C)/(D) be in the range of from 5/95 to 70/30. Of course, the peroxide composition of the present invention may also be prepared easily by reacting α,α-dimethylbenzyl alcohol with a mixture of (E) cumene hydroperoxide and (F) a hydroperoxide represented by the following formula:

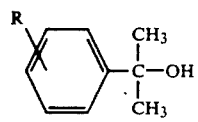

wherein R is as defined above, in the presence of an acid catalyst. It is preferred that the (E)/(F) weight ratio be in the range of from 5/95 to 70/30.

In the foregoing processes, the reaction ratio between the starting hydroperoxide and starting alcohol is not particularly critical, but ordinarily, it is preferred that the molar ratio of the starting alcohol to the starting hydroperoxide be in the range of from about 1.0 to about 1.3.

As the acid catalyst, there can be used, for example, silica-alumina, acid clay, silica-magnesia, alumina-boria, zinc chloride, aluminum sulfate, nickel sulfate, sulfuric acid and toluene-sulfonic acid. The amount used of the catalyst varies depending on the kind of the catalyst. For example, in case of a solid catalyst, it is used in an amount of 0.1 to 20% by weight, preferably 0.5 to 5% by weight. The reaction is carried out at a temperature of 20° to 110° C., preferably 50° to 80° C. It is preferred that the reaction be conducted in the absence of a solvent, but a solvent inert to the reaction, such as cumene, cymene or diisopropylbenzene, may be used. It is ordinarily preferred that water formed by the reaction be perpetually removed, though removal of water is not particularly critical when a certain kind of the catalyst is used. Removal of water can be accomplished according to known methods, for example, a method in which the reaction is carried out while an inert gas such as nitrogen is blown into the reaction vessel and water is removed in the state entrained by the inert gas, and a method in which the pressure in the reaction vessel is reduced to remove water by evaporation. Furthermore, there may be adopted a method in which a hydrocarbon solvent such as mentioned above is made present in the reaction vessel and water is removed by utilizing azeotropic distillation.

After completion of the condensation reaction between the alcohol and hydroperoxide, the acid catalyst used is removed from the reaction mixture by filtration or neutralization, and the reaction mixture is preferably washed with water. In order to perform these post treatments smoothly, especially to separate the oil phase from the aqueous phase conveniently at the water washing or neutralization step, it is preferred that the reaction mixture be diluted in advance with a low-boiling-point hydrocarbon, for example, a hydrocarbon having about 5 to about 8 carbon atoms. For example, pentane, hexane, cyclohexane and benzene are preferably employed. It is preferred that such hydrocarbon be used in an amount 1 to 10 times the amount of the resulting peroxide mixture based on the weight.

When such low-boiling-point hydrocarbon is used, it is removed by distillation after water washing. When the reaction mixture contains a high-boiling-point hydrocarbon such as cumene, cymene or diisopropylbenzene, such hydrocarbon is removed by steam distillation under reduced pressure. The recovered reaction mixture is subjected to concentration according to need and then to filtration if desired. Thus, the liquid peroxide composition of the present invention is obtained.

The peroxide composition of the present invention may also be prepared by reacting hydroperoxides such as mentioned above with α-methylstyrene and/or nucleus-alkylated α-methylstyrene. In this case, the intended peroxide mixture can be obtained in a high yield if the olefinic double bond/hydroperoxy group molar ratio is at least 2.

The peroxide composition of the present invention is valuable as a cross-linking agent for a high polymer. Since the peroxide composition of the present invention is different from DCP in that it is liquid at room temperature, when it is incorporated into a high polymer, a good metering property is attained and the compounding operation is advantageously performed very safely. Accordingly, a homogeneous molded article can be obtained very easily. Furthermore, since the peroxide composition of the present invention is liquid, incorporation of different matter can be effectively prevented, and incorporated different matter can easily be detected and removed. Moreover, since the thermal decomposition temperature of the peroxide composition of the present invention is relatively higher than that of DCP, the temperature for preliminary processing performed prior to cross-linking, for example, the high polymer extrusion temperature, can be elevated and therefore, the processability of the high polymer can be improved. Still further, the cross-linking efficiency is comparable to that attainable by the single use of DCP. Still in addition, since compounding of the liquid peroxide composition of the present invention with a high polymer in an extruder can be performed very easily, a homogeneous molded article can be obtained even if the extrusion molding is carried out at a high speed as in case of coating of wires.

As the high polymer that is cross-linked by the liquid peroxide composition of the present invention, there can be mentioned olefinic thermoplastic polymers and rubbery polymers. More specifically, there can be mentioned olefinic thermoplastic polymers such as medium-pressure polyethylene, low-pressure polyethylene, high-pressure polyethylene, poly-1-butene, ethylene-vinyl acetate copolymers, ethylene-acrylic acid ester copolymers, ethylene-propylene copolymers, ethylene-1-butene copolymers, ethylene-4-methyl-1-pentene copolymers and propylene-1-butene copolymers, and rubbery polymers such as ethylene-propylene copolymer rubber, butyl rubber, chlorinated polyethylene, silicone rubber and propylene-1-butene copolymer rubber. Furthermore, mixtures of at least two olefinic thermoplastic polymers, mixtures of at least two rubbery polymers and mixtures of at least one olefinic thermoplastic polymer with at least one rubbery polymer may be cross-linked by the peroxide composition of the present invention.

The liquid peroxide composition of the present invention is advantageously used not only for cross-linking of extrusion-molded articles of thermoplastic polymers or rubbery polymers such as mentioned above but also for production of cross-linked and foamed articles of thermoplastic polymers or rubbery polymers such as mentioned above.

Moreover, the liquid peroxide composition of the present invention can be used as a decomposition promotor for peroxide decomposition type polymeric compounds such as polypropylene and poly-4-methyl-1-pentene and as a polymerization initiator for radical polymerization.

The present invention will now be described in detail by reference to the following Examples that by no means limit the scope of the invention.

EXAMPLE 1

To a mixture of 152 g (1.0 mole) of cumene hydroperoxide, 40.8 g (0.3 mole) of α,α-dimethylphenylcarbinol, 105 g (0.7 mole) of α,α-dimethyl-m/p-tolylcarbinol (m/p=2/1) and 15 g of cumene was added 3.2 g of synthetic silica-alumina, and reaction was carried out at 60° C. for 4 hours while blowing nitrogen. A mixture of DCP and cumyl-m/p-cymyl peroxide (m/p=2/1) was obtained in a yield of 91%.

Then, 5 g of water was added to the reaction mixture and the synthetic silica-alumina was removed by filtration. The filtrate was concentrated by steam distillation under 30 to 100 mmHg at 75° C., and the concentrate was filtered to obtain 283 g of a peroxide mixture which was liquid at room temperature and in which the DCP/cumyl-m/p-cymyl peroxide weight ratio was 29/71. The so obtained peroxide mixture was characterized by an active oxygen amount of 5.25%, a purity of 92%, a specific gravity ($d_4^{25}$) of 1.01, a viscosity of 25.3 cp as measured at 25° C. Half life values for thermal decomposition are 116° C. (10 hours) and 179° C. (1 minute), respectively. Activation energy for thermal decomposition is 35.6 Kcal/mole.

EXAMPLE 2

Synthesis reaction was carried out in the same manner as described in Example 1 except that α,α-dimethyl-m-tolylcarbinol was used instead of α,α-dimethyl-m/p-tolylcarbinol used in Example 1, to obtain 280 g of a peroxide mixture in which the DCP/cumyl-m-cymyl peroxide weight ratio was 29/71. The so obtained peroxide mixture was characterized by an active oxygen amount of 5.23%, a purity of 91%, a specific gravity ($d_4^{25}$) of 1.01, a viscosity of 24.5 cp as measured at 25° C. Half life values for thermal decomposition are 115° C. (10 hours) and 178° C. (1 minute), respectively. Activation energy for thermal decomposition is 35.8 Kcal/mole.

EXAMPLES 3 TO 6

Peroxide mixtures of DCP and cumyl-m/p-cymyl peroxide (hereinafter abbreviated to "m/p-CCP") differing in the mixing ratio were synthesized in the same manner as in Example 1 except that the weight ratio of α,α-dimethyl-m/p-tolylcarbinol (m/p=2/1) to α,α-dimethylphenylcarbinol was changed as shown in Table 1. Properties of these peroxide mixtures are shown in Table 1.

TABLE 1

|  | Example 3 | Example 4 | Example 5 | Example 6 |
|---|---|---|---|---|
| m/p-CCP/DCP Weight Ratio | 90/10 | 80/20 | 60/40 | 40/60 |

TABLE 1-continued

|  | Example 3 | Example 4 | Example 5 | Example 6 |
|---|---|---|---|---|
| Active Oxygen Amount (%) | 5.02 | 5.13 | 5.36 | 5.54 |
| Specific Gravity ($d_4^{25}$) | 1.01 | 1.01 | 1.01 | 1.00 |
| Thermal Decomposition Data |  |  |  |  |
| for $t_{\frac{1}{2}}$ = 1 minute | 179 | 179 | 178 | 178 |
| for $t_{\frac{1}{2}}$ = 10 hours | 115 | 116 | 115 | 116 |
| Activation Energy (Kcal/mole) | 35.2 | 35.3 | 35.5 | 35.5 |

EXAMPLE 7

In the presence of 10 g of synthetic silica-alumina as a catalyst, 133 g (0.7 mole) of cumene hydroperoxide (having a purity of 80%) and 179 g (0.7 mole) of cymene hydroperoxide (having a purity of 65%) were reacted with 224 g (1.4 moles) of α,α-dimethylbenzyl alcohol (having a purity of 85%) at 60° C. for 5 hours while blowing nitrogen. A mixture of m/p-CCP and DCP was obtained in a yield of 93%.

To the so formed reaction mixture were added 2 l of hexane and 30 ml of water, and the synthetic silica-alumina was removed by filtration. The filtrate was washed with a 5% aqueous solution of NaOH and then with water. The oil layer was recovered and hexane was removed therefrom by distillation, and the residue was subjected to steam distillation under 30 to 50 mmHg at 65° C. and to concentration under 5 mmHg at 65° C. The concentrate was filtered to obtain a liquid peroxide mixture in which the DCP/m/p-CCP weight ratio was 55/45. The so obtained peroxide mixture was characterized by an active oxygen amount of 5.26%, a specific gravity ($d_4^{25}$) of 1.01, a viscosity of 21 cp as measured at 25° C. Half life values for thermal decomposition are 115° C. (1 minute) and 177° C. (10 hours), respectively. Activation energy for thermal decomposition is 35.6 Kcal/mole.

EXAMPLE 8

In the presence of 10 g of synthetic silica-alumina as a catalyst, 266 g (1.4 moles) of cumene hydroperoxide (having a purity of 80%) was reacted with 146 g (0.7 mole) of α,α-dimethyl-p-isopropylbenzyl alcohol (having a purity of 85%) and 112 g (0.7 mole) of α,α-dimethylbenzyl alcohol (having a purity of 85%) at 60° C. for 5 hours while blowing nitrogen. A mixture of DCP and α,α-dimethylbenzyl(α,α-dimethylbenzyl-p-isopropyl)peroxide [cumyl-p-isopropylcumyl peroxide] was obtained in a yield of 91%.

To the so obtained reaction mixture were added 2 l of hexane and 30 ml of water, and the synthetic silica-alumina was removed by filtration. The filtrate was washed with a 5% aqueous solution of NaOH and then with water. The oil layer was recovered and hexane was removed by distillation, and the residue was subjected to steam distillation under 30 to 50 mmHg at 65° C. and to concentration under 5 mmHg at 65° C. The concentrate was filtered to obtain a liquid peroxide mixture in which the DCP/cumyl-p-isopropylcumyl peroxide weight ratio was 45/55. The so obtained liquid peroxide mixture was characterized by an active oxygen amount of 4.95%, a purity of 90%, a specific gravity ($d_4^{25}$) of 1.00, a viscosity of 23 cp as measured at 25° C. Half life values for thermal decomposition are 114° C. (1 minute) and 176° C. (10 hours), respectively. Activation energy for thermal decomposition is 35.3 Kcal/mole.

EXAMPLE 9

To a mixture of 76 g (0.5 mole) of cumene hydroperoxide, 75 g (0.5 mole) of α,α-dimethyl-m-tolylcarbinol and 15 g of cumene was added 2 g of synthetic silica-alumina, and reaction was carried out at 60° C. for 3 hours while blowing nitrogen, to obtain cumyl-m-cymylperoxide in a yield of 90%.

The so obtained reaction mixture was filtered to remove the synthetic silica-alumina, and the filtrate was purified by silica gel column chromatography using benzene as an eluent. As a result, 118 g of cumyl-m-cymyl peroxide having a purity of 98% was obtained.

The so obtained peroxide was characterized by an active oxygen amount of 5.52%, a specific gravity ($d_4^{25}$) of 1.01, a viscosity of 27.5 cp as measured at 25° C. Half life values for thermal decomposition are 114° C. (10 hours) and 178° C. (1 minute), respectively. Activation energy for thermal decomposition is 35.2 Kcal/mole.

EXAMPLE 10

High-pressure polyethylene having a density of 0.91 and a melt index of 3.3 and the peroxide mixture synthesized in Example 1 or 2 were fed to an extruder, and the mixture was molten and kneaded and continuously extruded at 120° C. in the form of a strand having a diameter of 5 mm. The peroxide mixture was fed in an amount of 2.5 parts by weight per 100 parts by weight of the polyethylene, and further, an antioxidant was fed in an amount of 0.2 part by weight per 100 parts by weight of the polyethylene. The extruded strand was then cross-linked at 195° C. for 5 minutes in a cross-linking device.

In each case, continuous extrusion could be performed for a long time and the surface condition of the resulting strand was very good.

The gel fraction of the so formed strand (the insoluble substance content determined when the strand was dipped in xylene at 110° C. for 24 hours) was 83.8% (when the peroxide mixture of Example 1 was used) or 83.5% (when the peroxide mixture of Example 2 was used).

EXAMPLE 11

A composition comprising 100 parts by weight of low density polyethylene (LDPE) having a melt index of 3.3, 2 to 2.5 parts by weight of m/p-CCP, DCP or the peroxide mixture synthesized in Example 3, 4, 5 or 6 and 0.2 part by weight of an antioxidant was cross-linked (pressed) at 160° C. for 40 minutes. The gel fraction of the so formed press sheet (the insoluble substance content determined when the press sheet was dipped in xylene at 110° C. for 24 hours) was determined to obtain results shown in Table 2. Incidentally, the amount of the peroxide or peroxide mixture was adjusted within a range of 2 to 2.5 parts by weight so that the active oxygen amount was constant in each run.

TABLE 2

|  | m/p-CCP/DCP Weight Ratio | | | | | |
|---|---|---|---|---|---|---|
|  | 100/0 | 90/10 | 80/20 | 60/40 | 40/60 | 0/100 |
| Amount of peroxide or peroxide mixture (g/100 g of LDPE) | 2.5 | 2.4 | 2.3 | 2.2 | 2.1 | 2.0 |
| Gel fraction | 76.0 | 79.1 | 80.8 | 81.5 | 82.9 | 84.0 |

TABLE 2-continued

| | m/p-CCP/DCP Weight Ratio | | | | | |
|---|---|---|---|---|---|---|
| | 100/0 | 90/10 | 80/20 | 60/40 | 40/60 | 0/100 |
| (%) | | | | | | |

What we claim is:

1. A peroxide composition which is liquid at 25° C. and which can be used as a liquid cross-linking agent for high polymers, comprising (A) dicumyl peroxide and (B) a peroxide represented by the following general formula:

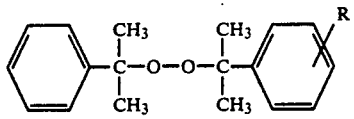

wherein R stands for an alkyl group having 1 to 3 carbon atoms,
at an (A)/(B) weight ratio of from 70/30 to 5/95.

2. A peroxide composition as set forth in claim 1 wherein dicumyl peroxide (A) and the peroxide (B) are contained at an (A)/(B) weight ratio of from 60/40 to 10/90.

3. A peroxide composition as set forth in claim 1 wherein the peroxide (B) is α,α-dimethylbenzyl(α,α-dimethyl-m-methylbenzyl)peroxide.

4. A peroxide composition as set forth in claim 1 wherein the peroxide (B) is α,α-dimethylbenzyl(α,α-dimethyl-p-methylbenzyl)peroxide.

5. A peroxide composition as set forth in claim 1 wherein the peroxide (B) is a mixture of α,α-dimethylbenzyl(α,α-dimethyl-m-methylbenzyl)peroxide and α,α-dimethylbenzyl(α,α-dimethyl-p-methylbenzyl)peroxide.

6. A process for the preparation of a peroxide composition comprising (A) dicumyl peroxide and (B) a peroxide represented by the following general formula:

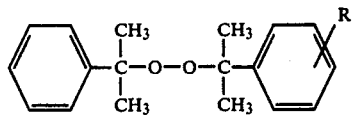

wherein R stands for an alkyl group having 1 to 3 carbon atoms,
at an (A)/(B) weight ratio of from 70/30 to 5/95, which comprises reacting cumene hydroperoxide with an alcohol mixture of (C) α,α-dimethylbenzyl alcohol and (D) an alcohol represented by the following general formula:

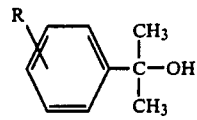

wherein R stands for an alkyl group having 1 to 3 carbon atoms,
in the presence of an acid catalyst, said peroxide composition being liquid at 25° C.

7. A process for the preparation of a peroxide composition comprising (A) dicumyl peroxide and (B) a peroxide represented by the following general formula:

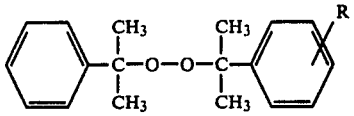

wherein R stands for an alkyl group having 1 to 3 carbon atoms,
at an (A)/(B) weight ratio of from 70/30 to 5/95, which comprises reacting α,α-dimethylbenzyl alcohol with a mixture of (E) cumene hydroperoxide and (F) a hydroperoxide represented by the following general formula:

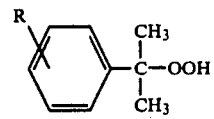

wherein R stands for alkyl group having 1 to 3 carbon atoms,
in the presence of an acid catalyst, said peroxide composition being liquid at 25° C.

8. A cross-linkable composition comprising 100 parts by weight of at least one high polymer selected from the group consisting of olefinic thermoplastic polymers and synthetic rubbery polymers, and 0.1 to 10 parts by weight of a cross-linking agent, said cross-linking agent consisting essentially of a peroxide composition comprising (A) dicumyl peroxide and (B) a peroxide represented by the following general formula:

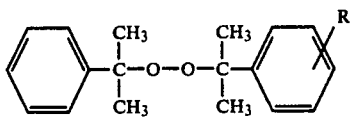

wherein R stands for an alkyl group having 1 to 3 carbon atoms,
at an (A)/(B) weight ratio of from 70/30 to 5/95.

* * * * *